United States Patent [19]

Bode et al.

[11] Patent Number: 4,686,238

[45] Date of Patent: Aug. 11, 1987

[54] PROCESS FOR THE PREPARATION OF HYDROCARBONS

[75] Inventors: Dirk Bode; Swan T. Sie, both of Amsterdam, Netherlands

[73] Assignee: Shell Oil Company, Houston, Tex.

[21] Appl. No.: 817,221

[22] Filed: Jan. 8, 1986

[30] Foreign Application Priority Data

Jan. 18, 1985 [NL] Netherlands ............... 8500121

[51] Int. Cl.$^4$ ............................................. C07C 1/04
[52] U.S. Cl. .................................. 518/700; 585/310; 208/108
[58] Field of Search ................ 518/700; 585/310; 208/108

[56] References Cited

U.S. PATENT DOCUMENTS

| 2,318,602 | 5/1943 | Duftschmid et al. | 518/700 |
| 4,413,063 | 11/1983 | Audibert et al. | 518/700 |
| 4,499,209 | 2/1985 | Hoek et al. | 518/715 |
| 4,522,939 | 6/1985 | Minderhoud | 502/242 |

FOREIGN PATENT DOCUMENTS

| 783061 | 3/1956 | United Kingdom . |
| 1548468 | 7/1979 | United Kingdom . |
| 2088407 | 11/1981 | United Kingdom . |
| 2130601 | 11/1983 | United Kingdom . |
| 2125062 | 2/1984 | United Kingdom . |
| 2161177 | 1/1986 | United Kingdom . |

OTHER PUBLICATIONS

Storch et al., Fischer Tropsch & Related Synthesis, John Wiley & Sons, New York, 1951, pp. 400–409.

Primary Examiner—Howard T. Mars

[57] ABSTRACT

A process for the preparation of hydrocarbons by reaction of carbon monoxide with hydrogen over a supported cobalt catalyst in a fixed bed reactor downflow operation with recycle of a heavy hydrocarbon liquid over the catalyst.

18 Claims, No Drawings

PROCESS FOR THE PREPARATION OF HYDROCARBONS

FIELD OF THE INVENTION

The invention relates to a process for the preparation of hydrocarbons by catalytic reaction of carbon monoxide with hydrogen.

BACKGROUND OF THE INVENTION

The preparation of hydrocarbons from an H$_2$/CO mixture by contacting this mixture at elevated temperature and pressure with a catalyst is known in the literature as the Fischer-Tropsch hydrocarbon synthesis process. Catalysts frequently used for the purpose contain one or more metals of the iron group together with one or more promoters and a carrier material. Suitable techniques for the preparation of these catalysts are such known techniques as precipitation, impregnation, kneading and melting. The products that can be prepared by using these catalysts usually have a very wide range of molecular weight distribution and, in addition to branched and unbranched paraffins, often contain considerable amounts of olefins and oxygen-containing organic compounds. Usually only a minor portion of the products obatined is made up of middle distillates. Of these middle distillates not only the yield but also the pour point is unsatisfactory. Therefore the direct conversion of H$_2$/CO mixtures according to Fischer-Tropsch is not a very attractive route for the production of middle distillates on a technical scale.

In this patent application "middle distillates" should be taken to be hydrocarbon mixtures whose boiling range corresponds substantially with that of the kerosene and gas oil fractions obtained in the conventional atmospheric distillation of crude mineral oil. The middle distillate range lies substantially between about 150° and 360° C.

Recently a class of Fischer-Tropsch catalysts was found which have the property of yielding a product in which only very minor amounts of olefins and oxygen-containing organic compounds occur and which consists virtually completely of unbranched paraffins, a considerable portion of which paraffins boils above the middle distillate range. It has been found that the high-boiling part of this product can be converted in high yield into middle distillates by means of hydrocracking. As feedstock for the hydrocracking at least the part of the product is chosen whose initial boiling point lies above the final boiling point of the heaviest middle distillate desired as end product. The hydrocracking, which is characterized by a very low hydrogen consumption, yields middle distillates with a considerably better pour point than those obtained in the direct conversion of an H$_2$/CO mixture according to Fischer-Tropsch.

The Fischer-Tropsch catalysts belonging to the above-mentioned class contain silica, alumina or silica-alumina as carrier material and cobalt together with zirconium, titanium, chromium and/or ruthenium as catalytically active metals in such quantities that the catalysts comprise 3-60 parts by weight of cobalt and 0.1-100 parts by weight of zirconium, titanium, chromium, and/or ruthenium per 100 parts by weight of carrier material. The catalysts are prepared by depositing the metals involved on the carrier material by kneading and/or impregnation. For further information on the preparation of these catalysts by kneading and/or impregnation reference may be made to U.S. Pat. No. 4,522,939 (Minderhoud et al).

SUMMARY OF THE INVENTION

Further investigation into the use of the above-mentioned cobalt catalysts in a vertical fixed bed reactor has now shown that the C$_3$+ selectivity of these catalysts can be improved when during the process a liquid which boils above 100° C. and consists substantially of one or more hydrocarbons is passed through the catalyst bed in a downward direction together with the feed gas. In order to achieve a considerable improvement in selectivity, there should be applied at the inlet of the catalyst bed a certain determined minimum superficial liquid flow velocity (V$_s$) which should be higher accordingly as the external surface area (S$_E$) of the catalyst is smaller. The relation between V$_s$ (in cm/s) and S$_E$ (in cm$^2$/ml) is rendered by $V_s \times S_E > 1$.

It is highly surprising that the favorable influence which is exercised on the catalyst selectivity by passing the liquid through the catalyst bed is not felt by iron catalysts prepared by impregnation and/or kneading, which are closely related to the present cobalt catalysts. On the contrary, comparative experiments with iron catalysts have shown that the C$_3$+ selectivity of these catalysts falls when said liquid is passed through the catalyst bed. A previous patent, U.K. Pat. No. 1,548,468 (Bijwaard et al), for a Fischer-Tropsch process, discloses the application of product recycle in a continuous wash of a promoted supported cobalt or iron catalyst to prevent activity decrease of the catalyst as a result of wax deposition. However, the Bijwaard patent provides no information or relationship between the superficial liquid velocity at the catalyst bed inlet (V$_s$) and the external surface of the catalyst.

Passing the liquid through the catalyst bed has the additional advantage of facilitating temperature control during the highly exothermal hydrocarbon synthesis.

In a further embodiment, the present invention relates to a process for the preparation of hydrocarbons by catalytic reaction of carbon monoxide and hydrogen. Specifically, the present invention deals with a process in which a mixture of carbon monoxide and hydrogen is contacted at elevated temperature and pressure with a catalyst comprising 3-60 parts by weight of cobalt and 0.1-100 parts by weight of at least one other metal chosen from zirconium, titanium, chromium and ruthenium per 100 parts by weight of silica, alumina or silica-alumina, where the catalyst has been prepared by kneading and/or impregnation. The catalyst is present in a vertical fixed bed reactor, the catalyst having an external surface area S$_E$, and in which during the process a liquid which boils above 100° C. and consists substantially of one or more hydrocarbons is passed through the catalyst bed in a downward direction together with the feed gas, at such a superficial liquid flow rate V$_s$ at the inlet of the catalyst bed that the relation $V_s \times S_E > 1$ (where V$_s$ is in cm/s and S$_E$ is in cm$^2$/ml).

The external surface area (S$_E$) of the catalyst can be found by taking a representative sample of a given volume expressed in ml and determining the external surface area expressed in cm$^2$ of each of the catalyst particles present therein, summing the external surface areas found, and dividing the sum by the volume of the sample. The internal surface area (S$_i$) of the catalyst is determined by means of nitrogen adsorption.

For the liquid which is passed through the catalyst bed during the process according to the invention use may very suitably be made of a portion of a heavy fraction which has been separated by distillation from the product obtained in the hydrocarbon synthesis, and/or which has been separated from the product obtained in an hydrocracking treatment if the hydrocarbon synthesis is followed by an hydrocracking treatment for the preparation of middle distillates. Said fraction which is partly used to be passed through the catalyst bed, may be either a distillate or a residual fraction. For instance, starting from the product obtained in the hydrocarbon synthesis or in the hydrocracking treatment, said product may be divided by distillation into a distillation fraction and a residual fraction boiling above 100° C., upon which a portion of the residual fraction is passed over the catalyst bed. Or, starting from the product obtained in the hydrocarbon synthesis or in the hydrocracking treatment, said product may be divided by distillation into a light distillation fraction, a middle distillation fraction boiling above 100° C. and a residual fraction, upon which a portion of the middle distillation fraction is passed over the catalyst bed. Preference is given to the use of a portion of a heavy fraction which has been separated by distillation from the product obtained in the hydrocarbon synthesis and in particular a portion of a residual fraction which has been separated from this product.

DETAILED DESCRIPTION OF THE INVENTION

In the process according to the invention it is preferred to use a catalyst of such an external surface area ($S_E$) between 5 and 70 cm$^2$/ml and such an internal surface area ($S_i$) between 10 and 400 m$^2$/ml as to satisfy the relation $10^6 > S_E^2 \times S_i > 2.5 \times 10^4$. The hydrocarbon synthesis using a catalyst which meets this requirement forms the subject of Netherlands Patent Application No. 8,402,149 which is commonly assigned copending U.S. patent application Ser. No. 749,896, filed June 28, 1985.

In the process according to the invention use is preferably made of the cobalt catalysts which form the subject matter of U.S. Pat. No. 4,522,939 which is incorporated by reference. These are catalysts which satisfy the relation $$(3 + 4R) > \frac{L}{S_i} > (0.3 + 0.4 R),$$

where
L = the total quantity of cobalt present on the catalyst, expressed in mg of Co/ml,
$S_i$ = the internal surface area of the catalyst, expressed in m$^2$/ml and
R = O if the catalyst is prepared by impregnation; and
R = the weight ratio between the quantity of cobalt applied to the catalyst by kneading and the total quantity of cobalt present n the catalyst, if the catalyst is prepared by kneading.

In the process according to the invention it is further preferred to use cobalt catalysts which have been prepared by any one of the following three procedures:
(a) cobalt is first applied by impregnation in one or more steps and subsequently the other metal is likewise applied by impregnation in one or more steps,
(b) the other metal is first applied by impregnation in one or more steps and subsequently cobalt is likewise applied by impregnation in one or more steps, and
(c) cobalt is first applied by kneading in one or more steps and subsequently the other metal is applied by impregnation in one or more steps.

In the process according to the invention it is further preferred to cobalt catalysts comprising 15–50 parts by weight of cobalt per 100 parts by weight of carrier. The quantity of the other metal preferably present in the cobalt catalysts depends on the manner in which this metal has been applied. In the case of catalysts where first the cobalt and then the other metal is applied to the carrier, preference is given to catalysts comprising 0.5–5 parts by weight of the other metal per 100 parts by weight of carrier. In the case of catalysts where first the other metal and then the cobalt is applied to the carrier, preference is given to catalysts comprising 5–40 parts by weight of the other metal per 100 parts by weight of carrier. For the other metal it is preferred to use zirconium and for the carrier it is preferred to use silica.

Preparatory to becoming eligible for use in the preparation of hydrocarbons from an $H_2$/CO mixture, the cobalt catalysts should be activated. This activation may suitably be carried out by contacting the catalysts at a temperature between 200° and 350° C. with hydrogen or a hydrogen-containing gas.

The conversion of the $H_2$/CO mixture inot hydrocarbons according to the invention is preferably carried out at a temperature of 125°–350° C. and in particular of 175°–275° C. and a pressure of 5–100 bar and in particular of 10–75 bar.

The process according to the invention is suitably carried out in one of the following types of reactors.
1. A reactor consisting of a pressure vessel in which are present vertical tubes containing the catalyst. In order to withdraw the reaction heat a coolant is passed along the exterior of the tubings.
2. A reactor substantially as that described above, but with the catalyst on the outside of the tubings and the coolant passing through the tubes. The tubes may be placed parallel to the flow direction of the synthesis gas as well as perpendicular to the flow direction, in the form of straight pipes or cooling spirals.
3. A reactor consisting of a pressure vessel containing the catalyst in a plurality of horizontal layers. After each transition of a catalyst layer the temperature of the reaction mixture which has risen owing to the reaction heat is cooled down, and subsequently the reaction mixture is passed through the following catalyst layer. Cooling can be achieved by means of heat exchangers or by admixture of cold synthesis gas and/or cold liquid.

$H_2$/CO mixtures which are suitable for conversion according to the invention into hydrocarbons can be very suitably obtained starting from light hydrocarbons such as methane by means of steam reforming or partial oxidation. Special preference is given to the use of natural gas as feedstock for the preparation of the $H_2$/CO mixture.

The $H_2$/CO mixture which is converted according to the invention into hydrocarbons preferably has an $H_2$/CO molar ratio higher than 1.5 and in particular an $H_2$/CO molar ratio between 1.75 and 2.25.

As has already been observed, when used for the conversion of an $H_2$/CO mixture the present cobalt catalysts yield a substantially paraffinic product whose high-boiling part can be converted in high yield into middle distillates by the use of a hydrocracking treatment. The feedstock chosen for the hydrocracking treatment is at least the part of the product whose initial boiling point lies above the final boiling point of the heaviest middle distillate desired as end product.

Although in the preparation of middle distillates from the product obtained over the cobalt catalyst the part of the product whose initial boiling point lies above the final boiling point of the heaviest middle distillate desired as end product will suffice as feed for the hydrocracking treatment, the total $C_5+$ fraction of the product prepared over the cobalt catalyst may also be used for the purpose, if desired.

The hydrocracking treatment is carried out by contacting the fraction to be treated at elevated temperature and pressure in the presence of hydrogen, with a catalyst containing one or more noble metals from Group VIII supported on a carrier. The hydrocracking catalyst used preferably is a catalyst comprising 0.2-1% w of platinum or palladium on silica-alumina as carrier. The hydrocracking treatment is preferably carried out at a temperature of 250°-350° C. and a pressure of 10-75 bar.

The invention is illustrated by the following example.

EXAMPLE

Three catalysts (catalysts 1-3) were prepared by single or two-step impregnation of three spherical silica carriers (silicas A-C) with aqueous solutions of metal compounds. At each impregnation step a quantity of solution was used of which the volume corresponded substantially with the pore volume of the carrier concerned. After each impregnation step the material was dried at 120° C. and calcined at 500° C. After the final calcination step the compositions were activated in hydrogen: catalysts 1 and 2 at 250° C. and catalyst 3 at 280° C. More details regarding catalysts 1-3 and their preparation follow here.

Catalyst 1

Single-step impregnation of silica A with a solution of cobalt nitrate in water, followed by single-step impregnation of the cobalt-loaded carrier with a solution of zirconium nitrate in water. Catalyst 1 comprised 25 parts by weight of cobalt and 0.9 parts by weight of zirconium per 100 parts by weight of silica and had an $S_E$ of 24 cm$^2$/ml.

Catalyst 2

This catalyst was prepared starting from silica B in the same manner as catalyst 1. Catalyst 2 comprised 25 parts by weight of cobalt and 0.9 parts by weight of zirconium per 100 parts by weight of silica and had an $S_E$ of 40 cm$^2$/ml.

Catalyst 3

Sinlge-step impregnation of silica C with an aqueous solution comprising iron nitrate, copper nitrate and potassium nitrate. Catalyst 3 comprised 25 parts by weight of iron, 1.25 parts by weight of copper and 1 part by weight of potassium per 100 parts by weight of silica and had an $S_E$ of 27 cm$^2$/ml.

Catalysts 1-3 were applied in nine experiments in the preparation of hydrocarbons from a mixture of carbon monoxide and hydrogen. To this end the H$_2$/CO mixture was passed in downward direction through a vertically arranged reactor containing a fixed catalyst bed. In some of the experiments the reaction product was separated by means of distillation into a distillation fraction and a residual fraction having an initial boiling point of 150° C., and part of the residual fraction was recirculated over the catalyst bed. The conditions under which the experiments were carried out and their results are given in Tables I and II.

Of the experiments named in the tables only experiments 3, 6 and 7 are experiments according to the invention. In these experiments such a liquid recirculation was applied as to satisfy the requirement $V_s \times S_E > 1$, and a considerable increase in $C_3+$ selectivity was obtained. Experiments 1, 2, 4, 5, 8 and 9 fall outside the scope of the invention. They have been included in the patent application for comparison. In experiments 1, 4 and 8 no liquid was passed over the catalyst bed. In experiments 2 and 5 liquid recirculation was applied, but without meeting the requirement $V_s \times S_E > 1$. In these experiments only a minor increase in $C_3+$ selectivity was attained. In experiment 9, which was carried out using an iron catalyst, a liquid recirculation was applied which did not meet the requirement $V_s \times S_E > 1$; nevertheless the $C_3+$ selectivity was seen to fall.

TABLE I

| Experiment No. | 1-3 | 4-7 | 8-9 |
|---|---|---|---|
| Catalyst No. | 1 | 2 | 3 |
| H$_2$/CO molar ratio of the feed | 2 | 1.85 | 2 |
| Temperature, °C. | 190 | 221 | 220 |
| Pressure, bar | 26 | 20 | 30 |
| Space velocity, Nl · l$^{-1}$ h$^{-1}$ | 850 | 650 | 1000 |

TABLE II

| Experiment No. | $V_s$, cm/s | CO conversion, % | $C_3+$ selectivity, % | $V_s \times S_E$ |
|---|---|---|---|---|
| 1 | 0 | 15 | 75 | 0 |
| 2 | 0.03 | 15 | 75.5 | 0.72 |
| 3 | 0.125 | 15 | 80 | 3 |
| 4 | 0 | 67 | 81 | 0 |
| 5 | 0.005 | 66 | 81.5 | 0.2 |
| 6 | 0.03 | 66 | 85 | 1.2 |
| 7 | 0.3 | 65 | 86 | 12 |
| 8 | 0 | 49 | 90 | 0 |
| 9 | 0.1 | 45 | 88 | 2.7 |

What is claimed is:

1. In a process for the preparation of hydrocarbons by the catalytic reaction of carbon monoxide with hydrogen comprising contacting a feed gas comprising a mixture of carbon monoxide and hydrogen at elevated temperature and pressure with a catalyst bed, in a vertical fixed bed reactor having an inlet of said catalyst bed, wherein the catalyst bed comprises a catalyst comprising from about 3 to about 60 parts by weight of cobalt and from about 0.1 to about 100 parts by weight of at least one other metal selected from the group consisting of zirconium, titanium, chromium and ruthenium supported on 100 parts by weight of catalyst carrier, and a catalyst carrier comprising a refractory oxide selected from the group consisting of silica, alumina and silica-alumina, and wherein the catalyst has an external surface area $S_E$, the improvement which consists of attaining an increased selectivity to $C_3+$ hydrocarbons by passing downwardly and concurrently with the feed gas through the vertical fixed bed reactor a liquid which boils above 100° C., and consists substantially of one or more hydrocarbons, at a superficial liquid flow velocity $V_s$ at the inlet of the catalyst bed to satisfy the the relation $V_s \times S_E > 1$, where $V_s$ is in cm/s and $S_E$ is in cm²/ml.

2. The process of claim 1, wherein the liquid which is passed through the catalyst bed during the process is part of a heavy fraction which boils above about 360° C. and has been separated by distillation from the product obtained in the hydrocarbon synthesis of the process.

3. The process of claim 1, wherein the liquid passed through the catalyst bed during the process is part of a heavy fraction which boils above about 360° C. and has been separated from the product obtained in an hydrocracking treatment for the preparation of middle distillates following the hydrocarbon synthesis of this process.

4. The process of claim 1 wherein the liquid passed through the catalyst bed during the process is a combination of a heavy fraction which boils above about 360° C. and has been separated by distillation from the product obtained in the hydrocarbon synthesis of this proces and a heavy fraction which boils above about 360° C. and has been separated from the product obtained in a hydrocracking treatment for the preparation of middle distillates following the hydrocarbon synthesis of this process.

5. The process of claim 1, wherein the liquid that is passed through the catatlyst bed during the process is part of a residual fraction which has been separated by distillation from the product obtained in the hydrocarbon synthesis of this process.

6. The process of claim 1 wherein the catalyst has an external surface area ($S_E$) between about 5 and about 70 cm²/ml and such an internal surface area ($S_i$) between about 10 and about 400 m²/ml as to satisfy the relation $10^6 > S_E^2 \times S_i > 2.5 \times 10^4$.

7. The process of claim 1 wherein the catalyst has L and $S_i$ as to satisfy the relation $$(3 + 4R) > \frac{L}{S_i} > (0.3 + 0.4 R),$$

where
L = the total quantity of cobalt present on the catalyst, expressed in mg of Co/ml,
$S_i$ = the internal surface area of the catalyst, expressed in m²/ml and
R = O if the catalyst is prepared by impregnation; and
R = the weight ratio between the quantity of cobalt applied to the catalyst by kneading and the total quantity of cobalt present n the catalyst, if the catalyst is prepared by kneading.

8. The process of claim 1 wherein the catalyst is prepared by the application of cobalt first to the catalyst carrier followed by application of the other metal(s) such that the catalyst comprises about 15 to about 50 parts by weight of cobalt and about 0.1 to about 5 parts by weight of other metal(s) per 100 parts by weight of carrier.

9. The process of claim 1 wherein the catalyst is prepared by application of the other metal(s) first to the catalyst followed by application of the cobalt such that the catalyst comprises about 15 to about 50 parts by weight of cobalt and about 5 to about 40 parts by weight of the other metal(s) per 100 parts by weight of carrier.

10. The process of claim 1 wherein the other metal is zirconium, and the carrier is silica.

11. The process of claim 1 wherein the temperature is about 125 to about 350° C. and the pressure is about 5 to about 100 bar.

12. The process of claim 1 wherein the temperature is about 175 to about 275° C. and the pressure is about 10 to about 75 bar.

13. The process of claim 1 wherein the $H_2/CO$ mixture has been obtained by steam reforming or partial oxidation of light hydrocarbons such as natural gas.

14. The process of claim 1 wherein the $H_2/CO$ mixture has an $H_2/CO$ molar ratio higher than 1.5.

15. The process of claim 1 wherein the $H_2/CO$ mixture has an $H_2/CO$ molar ratio of from about 1.75 to about 2.25.

16. The process of claim 1 wherein in order to prepare middle distillates from the product prepared over the cobalt catalyst, at least that portion of the product prepared over the cobalt catalyst of which the initial boiling point lies above the final boiling point of the heaviest middle distillate desired as end product is subjected to an hydrocracking treatment by contacting it at elevated temperature and pressure with a catatlyst comprising one or more noble metals from Group VIII supported on a carrier.

17. The process of claim 16 wherein in the hydrocracking treatment a catalyst is used which comprises 0.2–1 percent by weight of a metal selected from the group consisting of platinum or palladium, supported on silica-alumina as carrier.

18. The process of claim 16 wherein the hydrocracking treatment is carried out at a temperature of 250°–350° C. and a pressure of 10–75 bar.

* * * * *